US006840902B2

(12) United States Patent
Sano et al.

(10) Patent No.: US 6,840,902 B2
(45) Date of Patent: Jan. 11, 2005

(54) PORTABLE ENDOSCOPE

(75) Inventors: Hiroshi Sano, Chiba (JP); Yoshihiro Obata, Saitama (JP)

(73) Assignee: PENTAX Corporation, Tokyo (JP)

( * ) Notice: Subject to any disclaimer, the term of this patent is extended or adjusted under 35 U.S.C. 154(b) by 173 days.

(21) Appl. No.: 10/197,589

(22) Filed: Jul. 18, 2002

(65) Prior Publication Data

US 2003/0040658 A1 Feb. 27, 2003

(30) Foreign Application Priority Data

Aug. 21, 2001 (JP) .................................... P2001-249898

(51) Int. Cl.⁷ ............................................. A61B 1/12
(52) U.S. Cl. ...................... 600/158; 600/156; 600/159
(58) Field of Search ................................ 600/156, 157, 600/158, 159, 101; 220/562, 4.12, 4.14, 203.2

(56) References Cited

U.S. PATENT DOCUMENTS 5,830,128 A  * 11/1998 Tanaka ........................ 600/158

* cited by examiner

Primary Examiner—Beverly M. Flanagan
(74) Attorney, Agent, or Firm—Greenblum & Bernstein, P.L.C.

(57) ABSTRACT

A portable endoscope having a probe which is inserted into a human body, comprises a tank, a flexible tube, a pump, and a weight. The flexible tube is provided to supply liquid to the tip of the probe from the tank via a connection and a nozzle. The weight is provided to bend the flexible tube so that one end of the flexible tube, inside the tank, reaches the liquid regardless of the angle of inclination. A liquid and air supply unit for the endoscope is provided with the tank which stores liquid or cleansing water.

15 Claims, 9 Drawing Sheets

PORTABLE ENDOSCOPE

BACKGROUND OF THE INVENTION

1. Field of the Invention

The present invention relates to a portable endoscope which is capable of supplying liquid and gas for rinsing and cleaning an observing window.

2. Description of the Related Art

Conventionally, there is known an endoscope which has a light source, a water tank, and other peripheral devices. The light source supplies light to a distal end of a probe of the endoscope through a light guide. The water tank supplies water via a tube for rinsing and cleaning the observing window which protects the objective lens provided at the distal end of the probe.

Before operating the endoscope, the peripheral devices have to be carried to the place of operation and some have to be connected to electricity. Furthermore, the endoscope needs power cables so that the light source and other devices can be connected to a power socket. There are many problems concerning the portability of the endoscope and the peripheral devices, for example, the inconvenience of using many cables, and the limitation of the places where the endoscope can be used.

SUMMARY OF THE INVENTION

Therefore, an object of the present invention is to improve the portability and the ease of operation of a portable endoscope.

According to the present invention, a portable endoscope has a probe which is inserted into a human body. The portable endoscope comprises a tank, a flexible tube, a pump, and a weight. The tank stores liquid. The flexible tube extends from inside the tank to a liquid supply nozzle via a connection. The pump pumps the liquid to the distal end of the probe from the flexible tube. The weight is provided at one end of the flexible tube inside the tank, whereby, when the tank is inclined, the flexible tube is bent so that the end reaches the liquid regardless of the angle of inclination.

Further, according to the present invention, a portable endoscope comprises a tank, a flexible tube, a pump, and a weight, and further comprises an electric power source. The electric power source provides electricity for driving the pump and a light source. The tank, the pump, and the electric power source are provided in an operational unit of the portable endoscope.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention will be described below with reference to the embodiments shown in the drawings.

Figure 1:
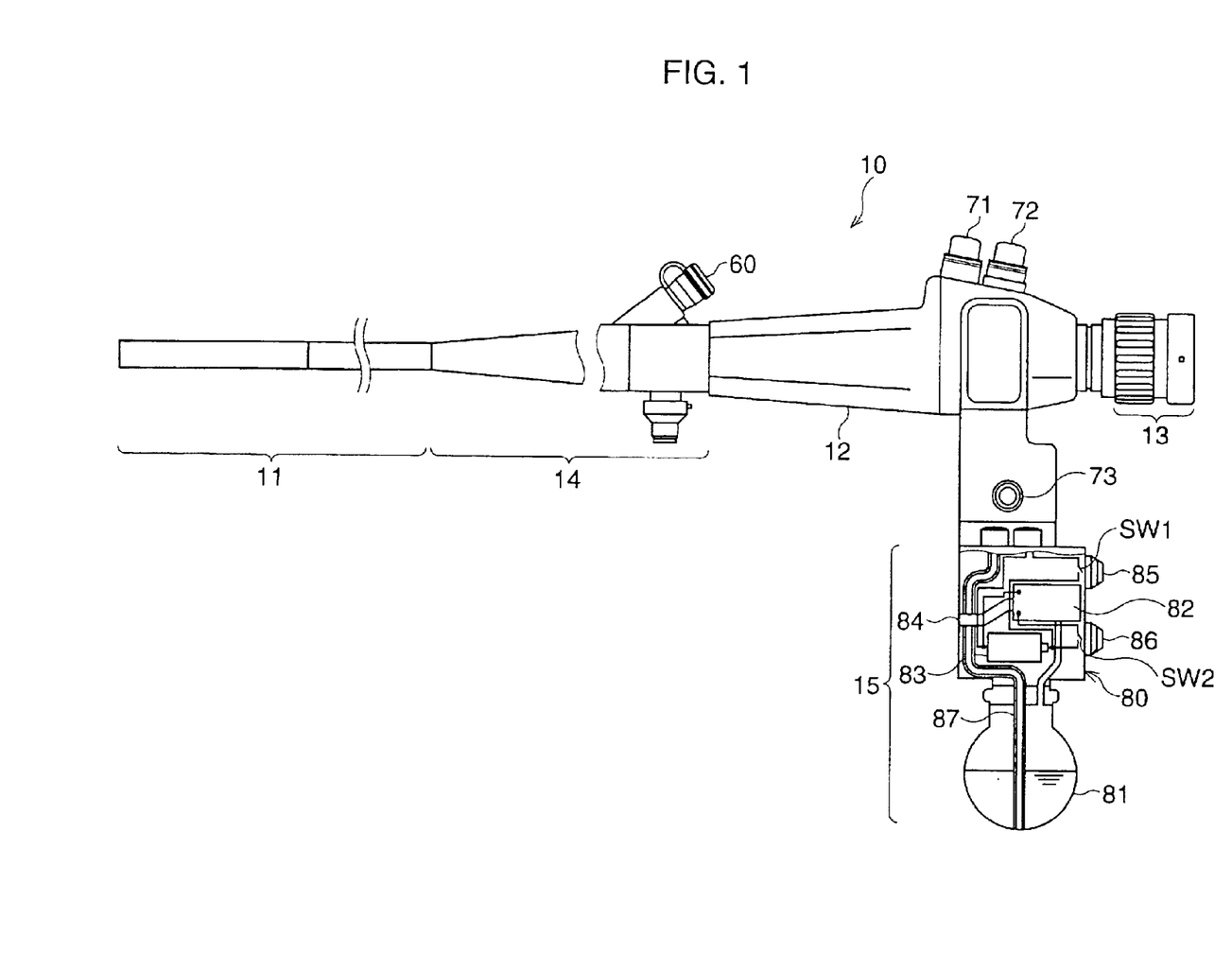
FIG. 1 is a side view of a portable endoscope having a probe to which a liquid and air supply unit of a first embodiment is attached.

FIG. 1 is a side and partially cross sectional view showing a portable endoscope having a probe. A fiberscope 10 is provided with a probe 11 which is a flexible duct that is inserted into a human body, an operational portion 12 which contains several operational buttons thereon, and an eyepiece portion 13 which is provided on the operational portion 12. An operational unit or a liquid and air supply unit 15 of a first embodiment is also attached to the operational portion 12. A connecting portion 14 connects the probe 11 and the operational portion 12.

Figure 2:
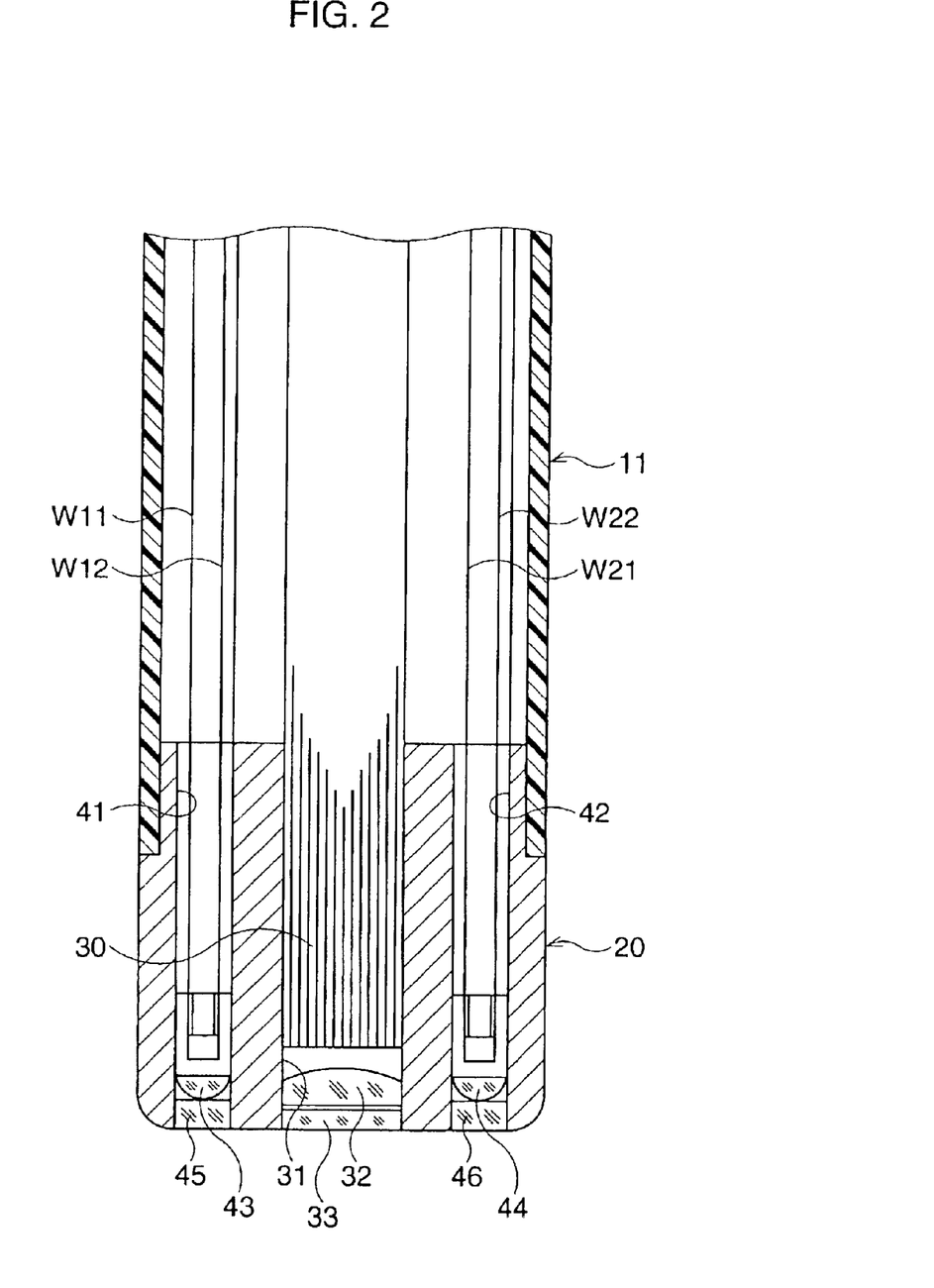
FIG. 2 is a cross sectional view showing the enlarged tip of the probe.

FIG. 2 is an enlarged cross sectional view of the tip of the probe 11. A tip body 20 which is made of an appropriate hard material such as corrosion resisting bearing metal, is fixedly adhered to the distal end of the probe 11. A hole 31 is provided in the tip to accommodate an image guide 30 which goes through the probe 11 and inside the tip body 20. The image guide 30 is a light fiber bundle for observing an object through the endoscope, and is equipped with an objective lens 32 at its distal end. An observing window 33 is fixed so as to cover the hole 31 to protect the objective lens 32 and to prevent foreign bodies from getting into the hole 31.

Furthermore, holes 41 and 42 are formed in the tip body 20 along a longitudinal axis. LEDs 43 and 44 are provided in the vicinity of the openings of the holes 41 and 42. Diverging lenses 45 and 46 are provided in front of the LEDs 43 and 44 inside the holes 41 and 42. Electrical wires W11, W12, W21, and W22 are provided to supply driving electricity for the LEDs 43 and 44.

Figure 3:
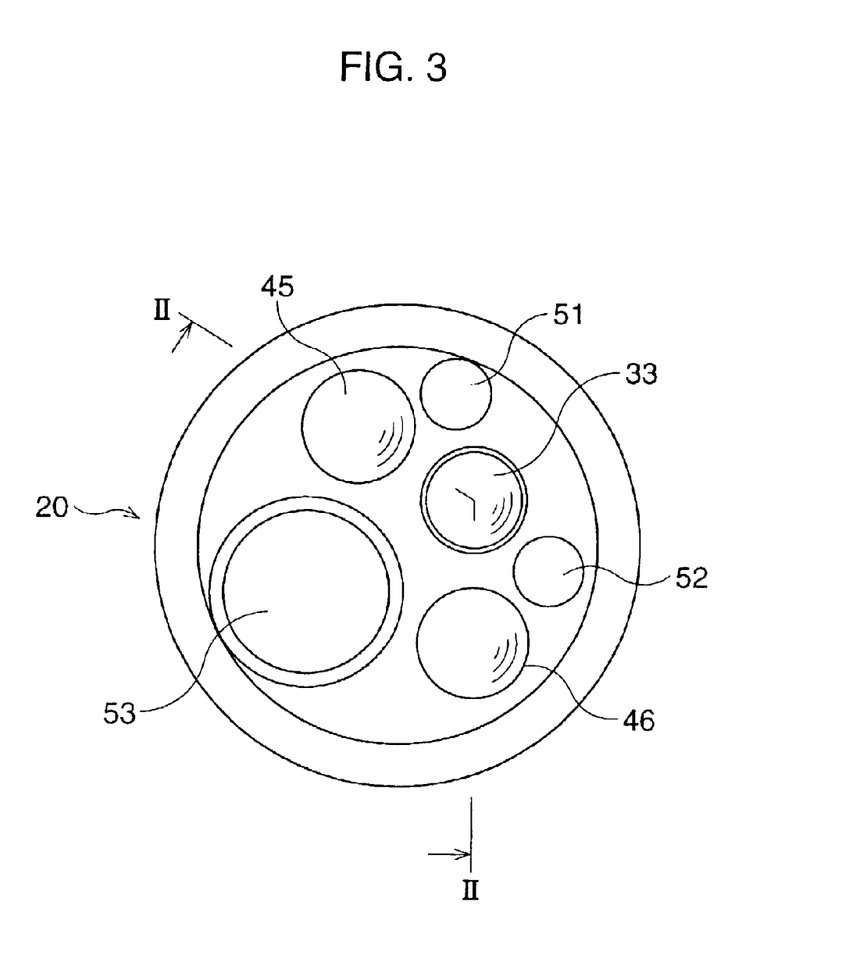
FIG. 3 is a front cross sectional view of the tip body.

FIG. 3 shows a front cross sectional view of the tip body 20 in which each part is viewed with relation to the position of each other part. FIG. 2 shows a cross sectional view along a line II—II of FIG. 3. An air supply nozzle 51 and a water and liquid supply nozzle 52 are respectively provided inside an air channel and a water and liquid channel (not shown) provided inside the probe 11. The air supply nozzle 51 is used to supply air or a gas to clean and dry the observing window 33, or to supply air into a human body. The water and liquid supply nozzle 52 is used to supply water or a liquid to rinse and clean the observing window 33. A treatment tool such as a biopsy forceps is provided through a forceps channel 53 to cut off an affected piece of tissue. The way in which air and liquid is supplied to the tip of the probe 11 will be described later.

In FIG. 1, a forceps opening 60 which is connected to the above mentioned forceps channel 53, is provided on the connecting portion 14. A treatment tool such as a biopsy forceps or a brush is inserted from the forceps opening 60 toward the tip of the probe 11 through the forceps channel 53.

An air and liquid supply button 71 and an absorption button 72 are provided on the operational portion 12. When a hole (not shown) on the top of the air and liquid supply button 71 is closed, air spouts from the air supply nozzle 51 (as shown in FIG. 3) to clean the observing window 33 which protects the objective lens 32, or to supply air into a human body. When the air and liquid supply button 71 is pressed down, liquid spouts from the liquid supply nozzle 52 (as shown in FIG. 3) of the tip body 20 to clean the observing window 33. When the absorption button 72 is pressed down, and the forceps opening 60 is equipped with a forceps lid (not shown), liquid or viscous material on the observing window 33 or air inside the human body is absorbed from the opening of the forceps channel 53 of the tip body 20 by an operation of an absorption device (not shown) using an absorption nipple 73.

The liquid and air supply unit 15 is provided near the absorption nipple 73. The liquid and air supply unit 15 is provided with a device 80 and a water tank 81 which stores the above mentioned liquid. The device 80 is provided on the opposite side of the air and liquid supply button 71 and the absorption button 72, and is perpendicular to the longitudinal direction, of the operational portion 12, and is fixed thereto. A partial conceptual cross sectional view of the device 80 is shown in FIG. 1.

The device 80 is provided with an air supply pump 82 and a battery 83. The air supply pump 82 is connected to an inlet 84 which is provided on a side wall of the device 80. The hole on the top of the air and liquid supply button 71, the air supply nozzle 51, and the water tank 81, are also connected to the inlet 84 through a tube or a pipe. The air supply pump 82 is a diaphragm pump provided to send air from the inlet 84 to the air and liquid supply button 71, the air supply nozzle 51, and the water tank 81. A battery 83 is an electric power source which supplies electricity to the air supply pump 82, and the LEDs 43 and 44 inside the tip body 20.

An LED button 85 to turn on and off the LEDs 43 and 44, and a pump button 86 to turn on and off the air supply pump 82 are provided on an outer side wall of the device 80. A switch SW1 is controlled to be turned on and off by the operation of the LED button 85. When the LED button 85 is pressed down with the switch SW1 being off, switch SW1 is turned on to start supplying driving electricity to the LEDs 43 and 44. As a result, the LEDs 43 and 44 are turned on causing light to be emitted from the tip through the diverging lenses 45 and 46. When the LED button 85 is pressed down again in this situation, ie. when switch SW1 is on, the switch SW1 is turned off so that the electricity is prevented from being supplied to the LEDs 43 and 44, so that they are turned off.

A switch SW2 is controlled to be turned on and off by the operation of the pump button 86. When the pump button 86 is pressed down with the switch SW2 being off, switch SW2 is turned on to start supplying driving electricity for the air supply pump 82. As a result, the air supply pump 82 starts drawing in air from the inlet 84 and sending it to the air and liquid supply button 71 and the air supply nozzle 51. When the pump button 86 is pressed down again in this situation, ie. when the switch SW2 is on, the driving electricity is prevented from being supplied to the air supply pump 82.

When using the fiberscope 10, the air supply pump 82 is always in operation. When the hole on the air and liquid supply button 71 is closed during the operation of the air supply pump 82, the air from the inlet 84 is supplied to the air supply nozzle 51 as mentioned above. When the air and liquid supply button 71 is pressed down, the air from the inlet 84 is sent through the air supply pump 82 to the water tank 81 only. As a result, the air pressure inside the tank 81 increases to push the liquid from the flexible tube 87 to the nozzle 52. Therefore, the liquid spouts from the liquid supply nozzle 52.

Figure 4:
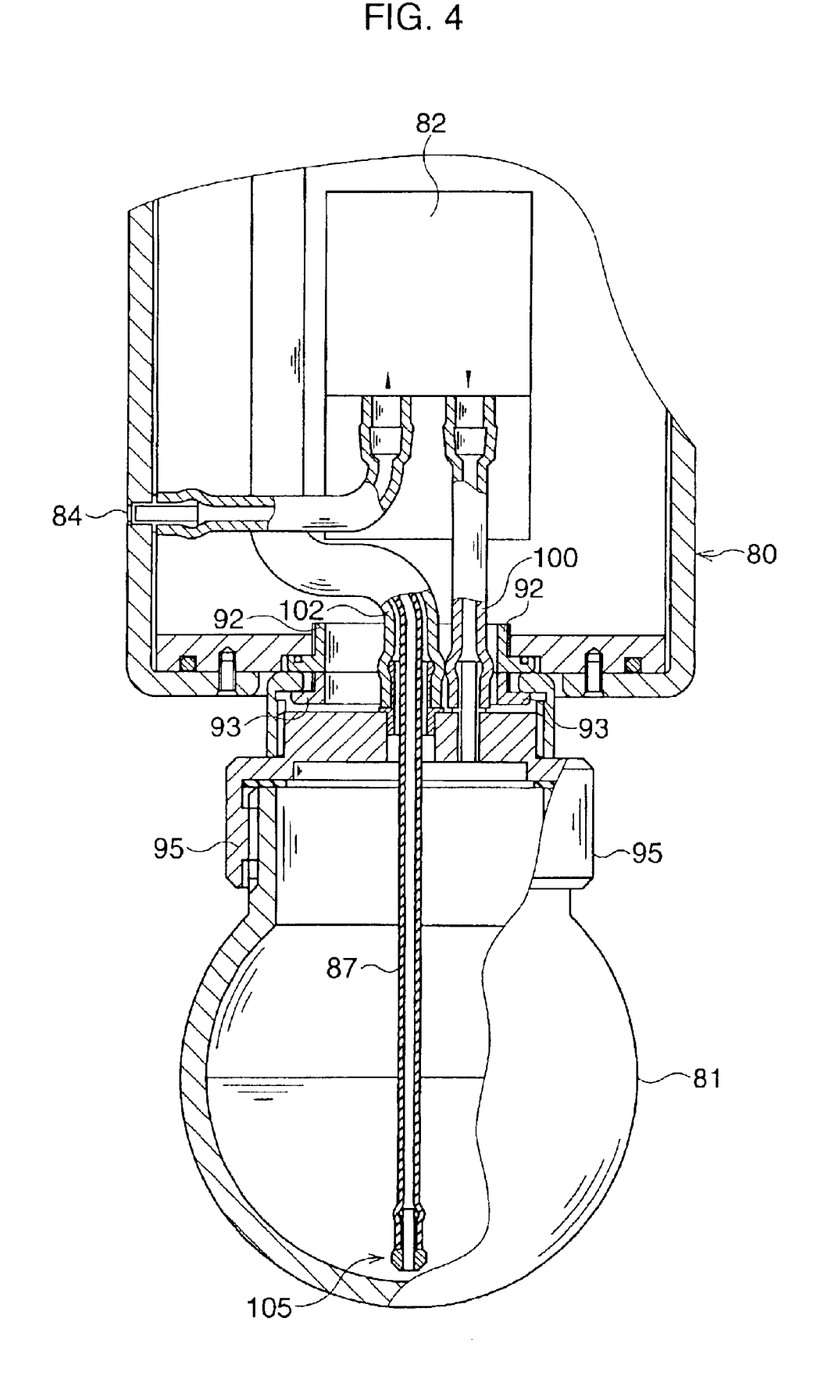
FIG. 4 is an enlarged cross sectional view of the water tank.

FIG. 4 shows an enlarged partial cross sectional view of the water tank 81. A tube holder 92 and a stopper 93 form a hole through which an air supply tube 100 connected to the air supply pump 82, an air supply tube 102 connected to the air supply nozzle 51, and the flexible tube 87 connected to the liquid supply nozzle 52, are inserted. The flexible tube 87 is provided inside the air supply tube (or pipe) 102. The air mentioned above goes through a gap between the flexible tube 87 and the air supply tube 102 to the tip of the probe 11.

The water tank 81 is a sphere as a whole. The flexible tube 87 is made of a flexible material such as silicon. When straightened, the flexible tube 87 has a length which is long enough to have its end approach an inner wall of the water tank 81. A weight 105 is provided at one end of the flexible tube 87 inside the water tank 81. The weight 105 is made of a metal which is resistant to chemical decomposition such as stainless steel.

Figure 5:
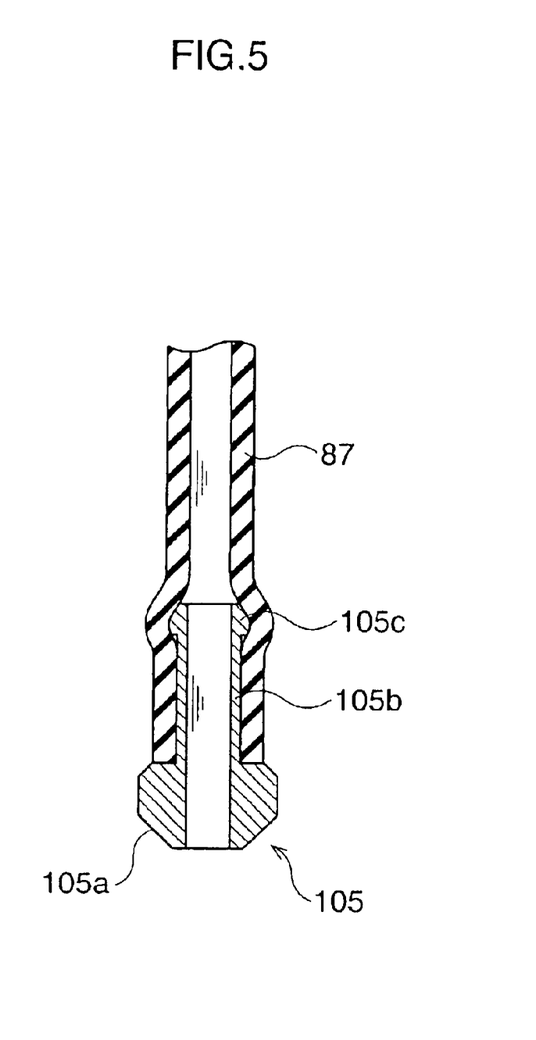
FIG. 5 is an enlarged view of one end of the flexible tube to which the weight is attached.

The weight 105 has three sections as can be seen in FIG. 5. A main section 105a formed to be nearly spherical, which is the largest tubular section providing the bulk of the weight; an insertion section 105b which is inserted into the flexible tube 87; and a deepest section 105c which has a circumference greater than an outer diameter of the insertion section 105b. The weight 105 has a main section 105a having an outer diameter larger than the inner diameter of the flexible tube 87 so as to prevent the main section 105a from being inserted into the flexible tube. The outer diameter of the insertion section 105b is the same or larger than the inner diameter of the flexible tube 87. The deepest section 105c has a circumference greater than an outer diameter of the insertion section 105b to prevent the weight 105 from separating from the flexible tube 87. The flexible tube is extendable when the weight 105 is inserted so as to grip the weight 105 tightly. As a result, the weight 105 is fixed to the end of the flexible tube 87. The weight 105 has a channel so that liquid can flow through the weight 105 and the flexible tube 87.

Figure 6:
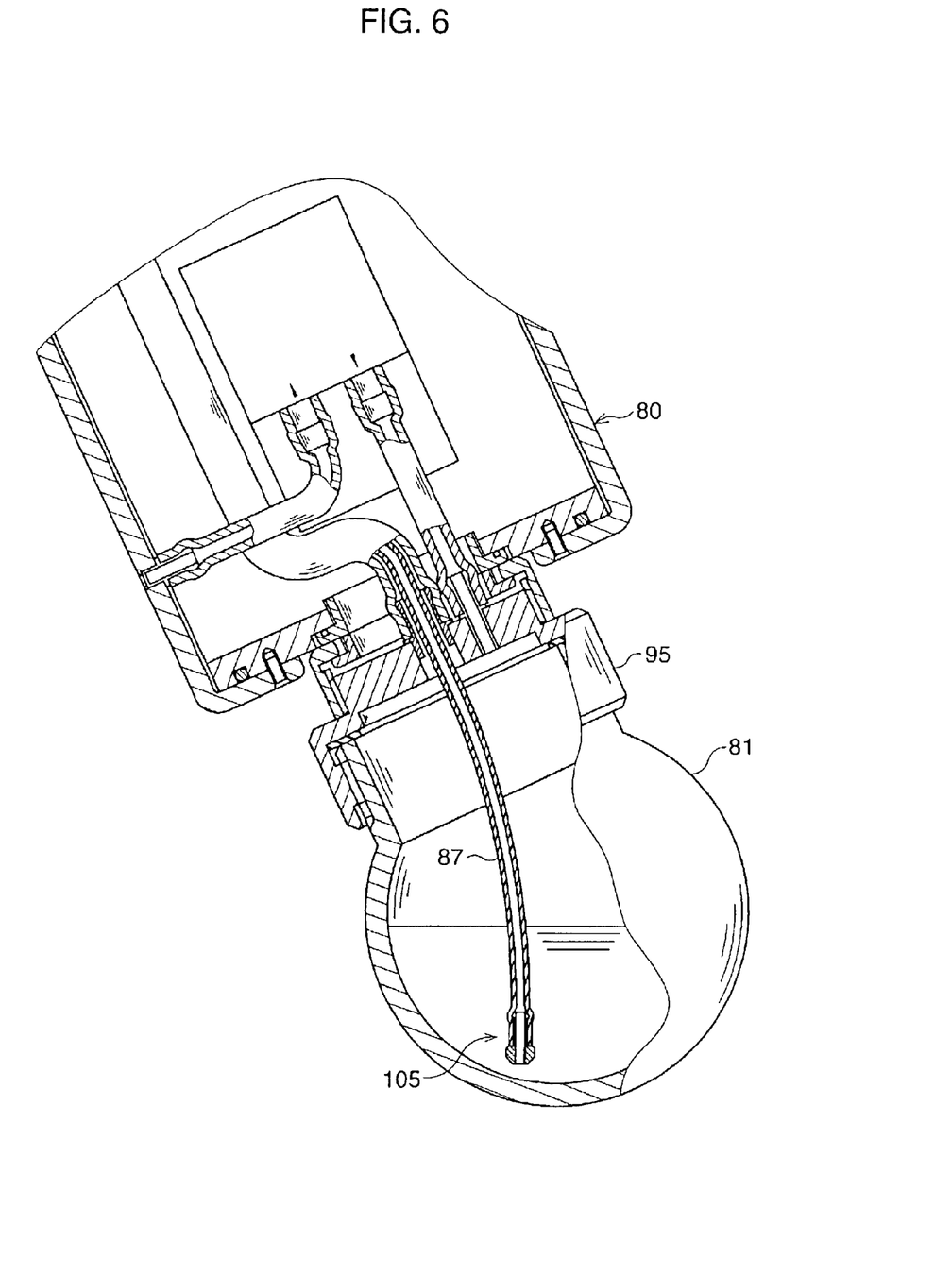
FIG. 6 is an enlarged view of the water tank when the operational portion is inclined.

As mentioned above, the flexible tube 87 is bendable having the weight 105 at one end. Therefore, when the water tank 81 and the operation portion 12 are inclined to whatever angle, the flexible tube 87 is bent so that the end reaches the liquid all the time regardless of the angle of inclination, providing good operational conditions for supplying liquid to the probe 11 of the fiberscope 10 as shown in FIG. 6.

Figure 7:
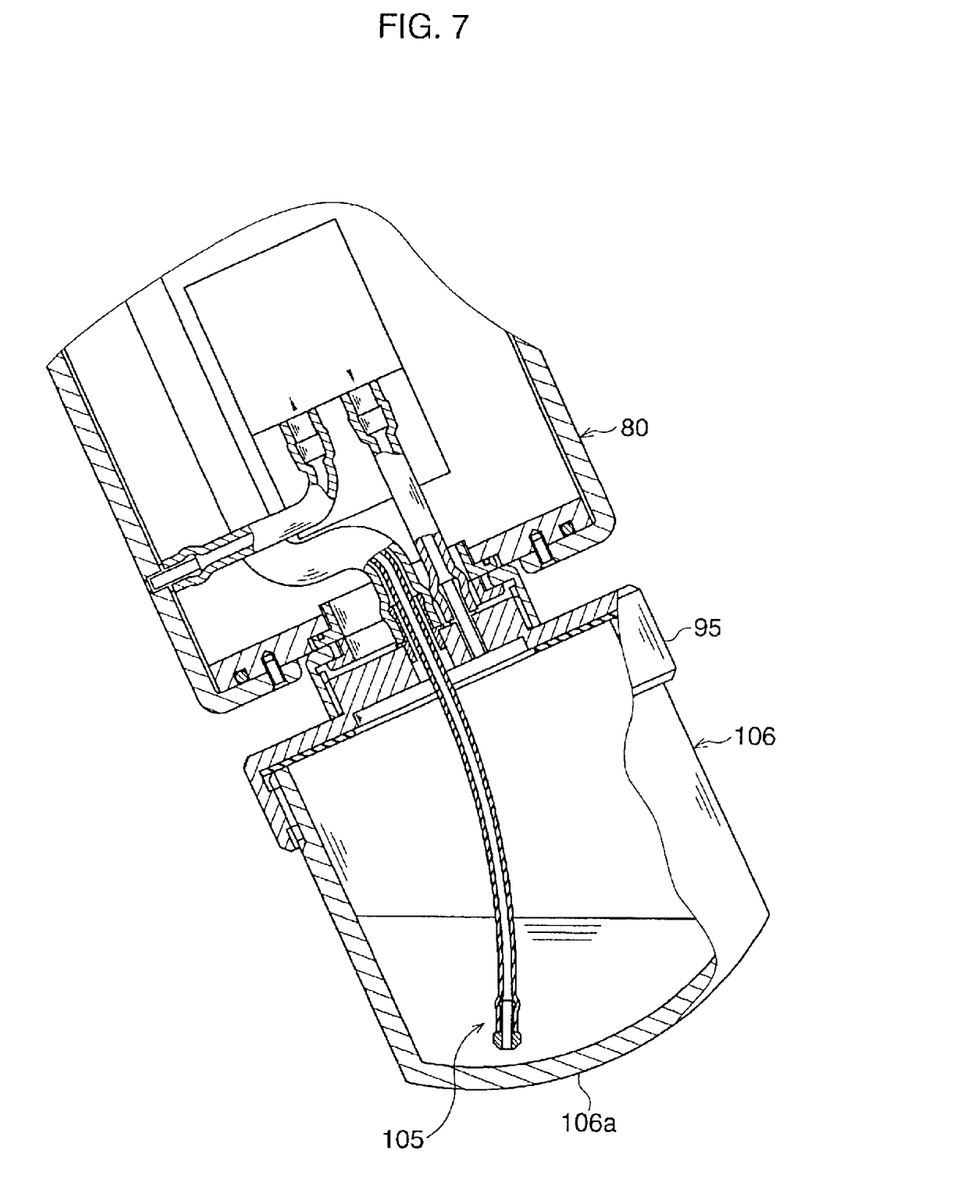
FIG. 7 is an enlarged view of another embodiment of the water tank.

Furthermore, the water tank 81 is a sphere in the first embodiment. Therefore, according to the inclination angle of the operation portion 12, the end of the flexible tube 87 inside the water tank 81 moves along the vicinity of the inner wall thereof. In other words, the end of the flexible tube 87 moves along the inner wall effectively relative to the change of the position of the operational portion 12. The water tank 81 need not be a sphere as a whole. For example, a tank 106 can be formed to be cylindrical for the main body and a sphere only at a bottom 106a which is formed at the opposite side of a tank lid 95 as shown in FIG. 7.

Figure 8:
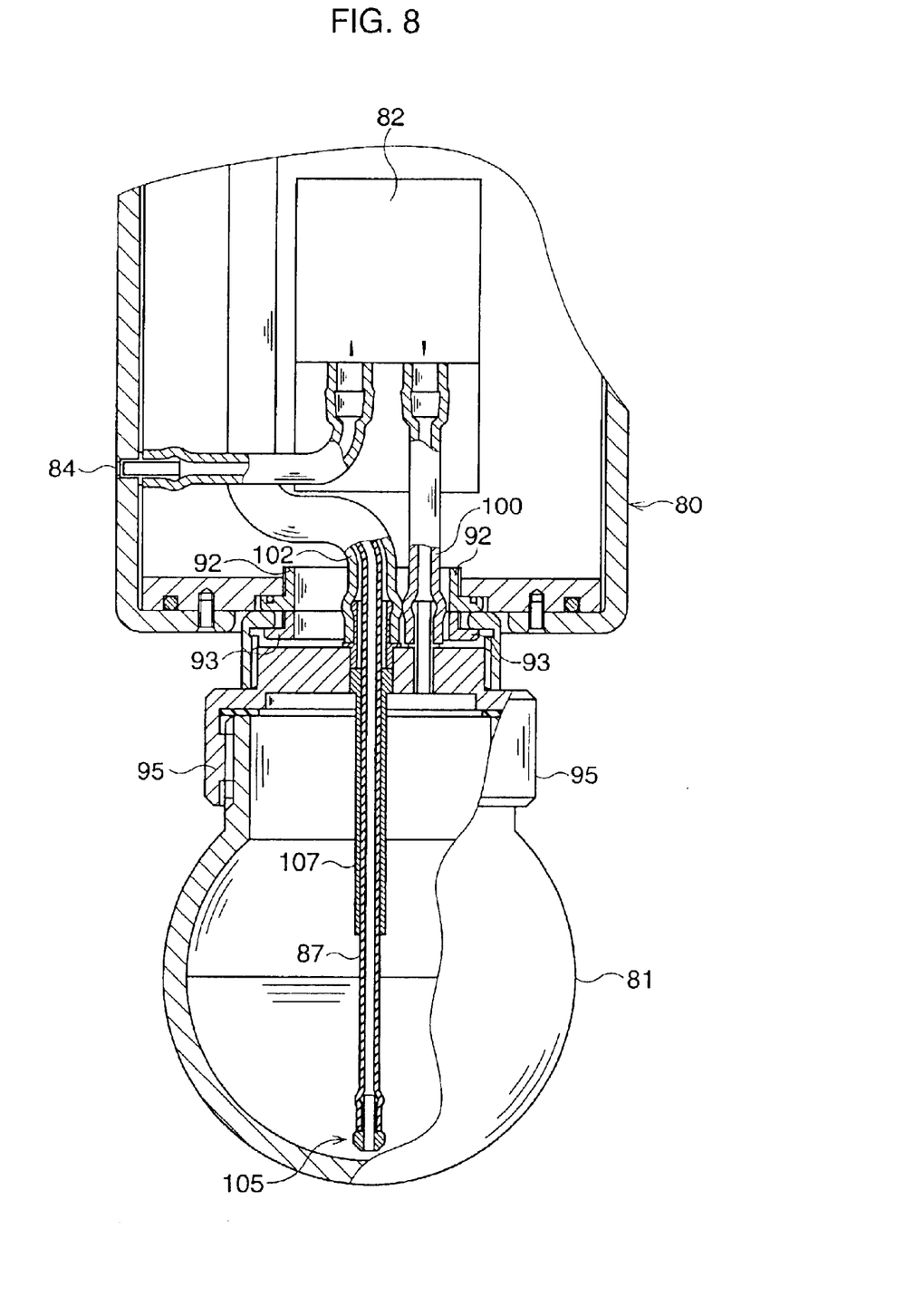
FIG. 8 is an enlarged partial cross sectional view of the water tank of the second embodiment.

FIG. 8 shows an enlarged partial cross sectional view of the water tank 81 of the second embodiment. The same numerical mark is given to the parts that are the same as those in the first embodiment. A rigid material 107 is made of metal such as stainless steel, formed to be cylindrical. The rigid material 107 extends from the tank lid 95 through to approximately the center of the water tank 81. Other parts are similar to those in the first embodiment.

Figure 9:
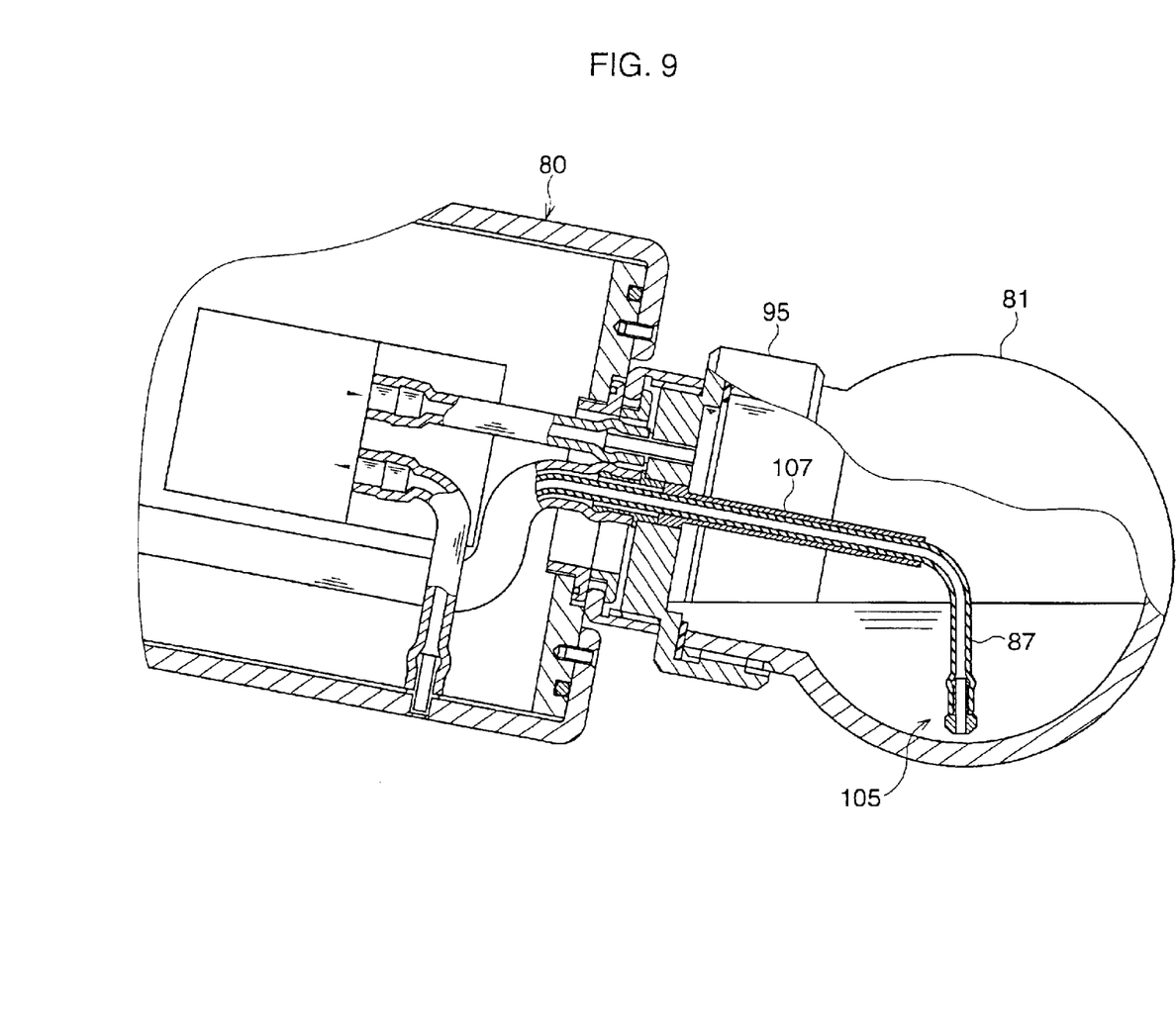
FIG. 9 is an enlarged view of the water tank when the operational portion is inclined.

As can be seen from FIG. 9, when the operational portion 12 is inclined, the flexible tube 87 is bent so as to be pivotable about one end of the rigid material, like the swing of a pendulum. As mentioned above, the end of the rigid material 107 is provided near the center of the water tank 81. In other words, the pivot point of the flexible tube 87, according to the movement of the operational portion 12, exists near the center of the spherical water tank 81. Therefore, regardless of the inclination of the operational portion 12, the end of the flexible tube 87 stays in the deepest portion of the liquid so that the flexible tube 87 is able to supply liquid to the probe 11 even when the amount of the liquid becomes low.

As mentioned above, according to the present invention, a flexible tube which is bendable has a weight at one end to stay in a liquid inside a tank regardless of the inclination of the operational portion during operation. Further, a device which supplies liquid and air is fixed to the operational portion. Therefore, the present invention is able to improve the portability and the ease of operation of a portable endoscope.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2001-249898 (filed on Aug. 21, 2001) which is expressly incorporated herein, by reference, in its entirety.

What is claimed is:

1. A portable endoscope having a probe which is inserted into a human body, comprising:
   a tank in which liquid is stored;
   a flexible tube that extends from the inside of said tank to supply liquid to said probe to rinse an element of the probe;
   a pump that supplies said liquid to a tip of said probe;
   a weight that is provided at one end of said flexible tube inside of said tank, whereby, when said tank is inclined, said flexible tube is bent so that said end reaches said liquid regardless of the angle of inclination.

2. A portable endoscope according to claim 1, wherein said tank is formed to be a partial sphere.

3. A portable endoscope according to claim 1, wherein said tank is formed to be a sphere.

4. A portable endoscope according to claim 1, wherein said tank is formed to be a sphere only at a bottom portion of said tank.

5. A portable endoscope according to claim 1, wherein said flexible tube is provided inside of a pipe, so that air can be supplied through a gap between said pipe and said flexible tube.

6. A portable endoscope according to claim 1, wherein said flexible tube has a length which is long enough to have said end of said tube approach an inner wall of said tank.

7. A portable endoscope according to claim 6, wherein said end moves along said inner wall relative to the inclination.

8. A portable endoscope according to claim 7, wherein part of said flexible tube is covered by a rigid material to change the position of a pivot point of said flexible tube form the side of said tank to a predetermined point inside of said tank.

9. A portable endoscope according to claim 8, wherein said predetermined part is located near the center of said tank.

10. A portable endoscope according to claim 1, wherein said weight is made of a metal which is resistant to chemical decomposition.

11. A portable endoscope according to claim 10, wherein said metal is stainless steel.

12. A portable endoscope according to claim 1, wherein said weight is formed to be tubular comprising three sections; a main section which is the largest spherical section, providing a bulk of said weight; an insertion section which is inserted into said flexible tube; and a deepest section having a circumference greater than an outer diameter of said insertion section to prevent said weight from separating from said flexible tube.

13. A portable endoscope according to claim 12, wherein said weight comprises said main section having an outer diameter larger than an inner diameter of said flexible tube so as to prevent said main section from being inserted into said flexible tube.

14. A portable endoscope according to claim 12, wherein said outer diameter of said insertion section is the same or larger than said inner diameter of said flexible tube.

15. A portable endoscope having a probe which is inserted into a human body, comprising:
   a tank in which liquid is stored;
   a flexible tube that extends from the inside of said tank to supply liquid to said probe to rinse an element of the probe;
   a pump that supplies said liquid to a tip of said probe;
   a weight that is provided at one end of said flexible tube inside of said tank, whereby, when said tank is inclined, said flexible tube is bent so that said end reaches said liquid regardless of the angle of inclination; and
   an electric power source that provides driving electricity for said pump and a light source which is provided at said tip of said probe;
   said tank, said pump, and said electric power source being provided in an operational unit of said portable endoscope.

* * * * *